United States Patent
Sage, Jr. et al.

[11] Patent Number: 5,843,015
[45] Date of Patent: *Dec. 1, 1998

[54] MOLECULES FOR IONTOPHORETIC DELIVERY

[75] Inventors: Burton H. Sage, Jr., Raleigh; Randal A. Hoke, Cary, both of N.C.

[73] Assignee: Becton Dickinson and Company, Franklin Lakes, N.J.

[*] Notice: The term of this patent shall not extend beyond the expiration date of Pat. No. 5,494,679.

[21] Appl. No.: 797,436

[22] Filed: Feb. 10, 1997

Related U.S. Application Data

[63] Continuation of Ser. No. 579,993, Dec. 28, 1995, which is a continuation of Ser. No. 174,589, Dec. 28, 1993, Pat. No. 5,494,679.

[51] Int. Cl.$^6$ ..................................................... A61N 1/30
[52] U.S. Cl. ................................................................. 604/20
[58] Field of Search .............................. 604/20; 424/449, 424/443, 447; 607/115

[56] References Cited

U.S. PATENT DOCUMENTS

| | | | |
|---|---|---|---|
| 4,731,049 | 3/1988 | Parsi | 604/20 |
| 5,203,768 | 4/1993 | Haak et al. | 604/20 |
| 5,376,107 | 12/1994 | Inagi et al. | 604/20 |
| 5,494,679 | 2/1996 | Sage, Jr. et al. | 604/20 |

*Primary Examiner*—Mark Bockelman
*Attorney, Agent, or Firm*—Susan A. Capello; David T. Banchik

[57] ABSTRACT

The present invention relates to a method for preparing proteins or peptides for iontophoretic delivery by modifying said proteins or peptides, by hydrophobic bonding of acharged molecule to a hydrophobic region of the protein or peptide, to have an isoelectric point of less than about 4.0 or greater than about 7.3 with an electrostatic charge of at least plus or minus 1 over the pH range of about 4.0 to about 7.3. Another embodiment of the present invention relates to a device for delivery of a protein or peptide having an isoelectric point of less than about 4.0 or greater than about 7.3 with an electrostatic charge of at least plus or minus 1 over the pH range of about 4.0 to about 7.3.

4 Claims, 6 Drawing Sheets

MOLECULES FOR IONTOPHORETIC DELIVERY

This application is a continuation of prior application Ser. No. 08/579,993 pending, filed Dec. 28, 1995, which in turn is a continuation of application Ser. No. 08/174,589 filed Dec. 28, 1993, now issued as U.S. Pat. No. 5,494,679.

FIELD OF INVENTION

The invention is in the field of peptide and protein drug delivery. In particular the invention is in the field of Iontophoretic peptide and protein drug delivery.

BACKGROUND OF INVENTION

The recent developments in molecular biology have provided great amounts of useful peptides and proteins. Not only are previously minuscule amounts of certain peptides and proteins now available in large quantities but new and modified forms of peptides and proteins are readily available. In conjunction with recent availability, the biological and therapeutic importance of peptides and proteins has enjoyed increased appreciation. Peptides and proteins are particularly susceptible to degradation when administered by routes other than parenteral. These non-parenteral routes of administration subject the peptides and proteins to gastrointestinal incompatibility (e.g., degradation by proteolytic enzymes) and hepatic "first pass" metabolism in addition to creating varying concentration amounts of the peptide or protein in the blood (i.e., circulating levels). The traditional non-parenteral routes of administration, therefore, are most often ineffective.

Parenteral administration is usually required to achieve therapeutic levels of peptides and proteins. However, peptides and proteins are inherently short acting, thereby requiring frequent injections. The frequent injections subject a patient to additional pain and potential non-compliance and health hazards. Alternative means to administer peptide and protein drugs is an active area of research. One notable means for peptide and protein drug delivery is iontophoresis iontophoresis refers to the transport of ionic solutes through biological membranes under the influence of an electric field. Iontophoretic drug delivery has the ability to bypass the gastrointestinal and hepatic first pass obstacles that render enteral routes of peptide and protein administration of relative little effectiveness. lontophoresis however, has yet to demonstrate wide-spread success in peptide and protein delivery. However, proteins and peptides appropriate for electrolytic delivery have been described in U.S. Pat. No. 4,940,456 and U.S. Pat. No. 4,878,892, respectively. However, methods for delivering peptides and proteins by iontophoresis are still cumbersome and require many steps and additions of extraneous materials that are not well-suited for simple and efficient iontophoretic delivery. Peptides and proteins for iontophoretic delivery and methods for modifying peptides and proteins for iontophoretic delivery are still mostly unmet.

SUMMARY

The present invention provides peptides and proteins for iontophoretic delivery. Embodiments of the invention include modified peptides and proteins for iontophoretic delivery.

One embodiment of the present invention provides for an iontophoretic device for the delivery of the proteins or peptides having specific characteristics. The iontophoretic device has:

(a) a current distributing member;

(b) an ionized substance reservoir containing a protein or peptide which may or may not have been modified and which is ionized or capable of being ionized (herein after known as an "proteins or peptides") in electrical communication with the current distributing member and adapted to be placed in ionic communication with the epithelial surface;

(c) an electrolyte reservoir containing an electrolyte, in electrical communication with an indifferent electrode and in ionic communication with an epithelial surface;

(d) an electrical power source in current delivering connection with the current distribution member and the electrolyte reservoir.

Other embodiments include methods for delivering peptides and proteins by iontophoresis and patches comprising peptides and proteins for delivery by iontophoresis. Specific embodiments include the treatment of disease states and afflictions by iontophoretic delivery of peptides and proteins.

The advantages of iontophoretic delivery are many. The invention provides a means for rapid delivery and rapid termination of protein and peptide administration. A peptide or protein with a short activity period is also deliverable by practicing the present invention. The invention also eliminates the potential for overdosing or underdosing a peptide or protein. The problems associated with the "first pass" gastrointestinal and hepatic systems associated with oral administration is also eliminated, and the risks and inconveniences inherent in parental therapies is avoided. As used in this document, "patient" refers to animals, including humans; household animals such as dogs and cats, livestock such as cattle, horses, sheep, pigs, goats and rabbits; laboratory animals such as mice and rats; and zoo animals such as exotic species The term "patch" as used in this document, refers to the variety of containment means for drug delivery by iontophoresis in general as well as specifically for peptides and proteins. Such means include, but is not limited to, bandages, pre-filled passive drug delivery patches, pre-filled iontophoretic drug delivery devices, pre-filled active drug delivery patches, and reusable iontophoretic drug delivery devices comprising a drug reservoir that is reusable or refillable.

DESCRIPTION OF THE INVENTION

An embodiment of the present invention relates to an iontophoretic device for non-invasively administrating a therapeutic concentration of a protein or peptide which has or has been modified to have an isoelectric point of less than about 4.0 or greater than about 7.3 with at least an electrostatic charge of plus or minus 1 over the pH range of about 4.0 to about 7.3 which is or is capable of being ionized (hereinafter "protein(s) or peptide(s)") a patient:

(a) a current distributing member;

(b) an ionized substance reservoir containing a protein or peptide, in electrical communication with the current distributing member and adapted to be placed in ionic communication with the epithelial surface; and (c) an electrolyte reservoir containing an electrolyte, in electrical communication with an indifferent electrode and in ionic communication with the epithelial surface;

(d) an electrical power source in current delivering connection with the current distribution member and the electrolyte reservoir.

The iontophoretic device of the present invention may by way of example and not limitation include the following component and materials.

A. The Current Distributing Member (active electrode)

The iontophoretic electrode of the invention includes a current distributing member which conveys electrical current into the iontophoretic reservoirs for the delivery of an ionized substance. The current distributing member is constructed of any of a large variety of electrically conductive materials, including both inert and sacrificial materials.

Inert conductive materials are those electrically conductive materials which, when employed in the iontophoretic devices of the invention, do not themselves undergo or participate in electrochemical reactions. Thus, an inert material distributes without being eroded or depleted due to the distribution of current, and conducts current through the generating ions by either reduction or oxidation of water. Inert conductive materials typically include, for example, stainless steel, platinum, gold, and carbon or graphite.

Alternatively, the current distributing member may be constructed from a sacrificial conductive material. A material may be considered sacrificial if, when employed as an electrode in an iontophoretic device of the invention, the material is eroded or depleted due to its oxidation or reduction. Such erosion or depletion occurs when the materials and formulations used in the iontophoresis device enable a specific electrochemical reaction, such as when a silver electrode is used with a formulation containing chloride ions. In this situation, the current distributing member would not cause electrolysis of water, but would itself be oxidized or reduced.

Typically, for anodes, a sacrificial material would include an oxidizable metal such as silver, zinc, copper, etc. In contrast to the hydroxyl and hydronium ions electrochemically generated via an inert material, the ions electrochemically generated via a sacrificial material would include metal cations resulting from oxidation of the metal. Metal/metal salt anodes may also be employed. In such cases, the metal would oxidize to metal ions, which would then be precipitated as an insoluble salt.

For cathodes, the current distributing member may be constructed from any electrically conductive material provided an appropriate electrolyte formulation is provided. For example, the cathodic current distributing member may be constructed from a metal/metal salt material. A preferred cathodic material is a silver/silver halide material. In such embodiments, a metal halide salt is preferably employed as the electrolyte. In this case, the device would electrochemically generate halide ions from the electrode as the metal is reduced. Also, accompanying silver ions in a formulation would be reduced to silver metal and would deposit (plate) onto the electrode. In other embodiments, the cathode material may be an intercalation material, an amalgam, or other material which can take electrolyte cations such as sodium out of solution, below the reduction potential of water. In addition, other materials may be used which permit the plating out of a metal from the appropriate electrolyte solution. Thus, metals such as silver, copper, zinc, and nickel, and other materials, such as carbon, may be employed when an appropriate metal salt such as silver nitrate or zinc sulfate is in solution in the electrolyte reservoir. While such materials may develop increased resistivity as a metal plates out during use, they are not eroded or depleted during use as cathodic current distributing members. They are therefore not strictly "sacrificial" in this context.

Additional types of materials useful as current distributing members according to the invention are disclosed in detail in a co-pending application entitled Low-Cost Electrodes for an Iontophoretic Device, by V. Reddy et al., Ser. No. 08/536,029, filed on Sep. 29, 1995 (Attorney Docket P-3066), the disclosure of which is incorporated by reference herein.

The current distributing member may take any form known in the art, such as the form of a plate, foil layer, screen, wire, or dispersion of conductive particles embedded in a conductive matrix.

B. The Electrolyte Reservoir

1. Electrolytes

In the iontophoretic devices of the invention, an electrolyte reservoir is arranged in electrical communication with a current distributing member. Typically, electrical communication requires that electrons from the current distributing member are exchanged with ions in the electrolyte reservoir upon the application of electrical current. Such electrical communication is preferably not impeded to any excessive degree by any intervening material(s) used in the construction of the iontophoretic device. In other words, the resistivity of the interface is preferably low.

The electrolyte reservoir comprises at least one electrolyte, i.e., an ionic or ionizable component which can act to conduct current toward or away from the current distributing member. Typically, the electrolyte comprises one or more mobile ions, the selection of which is dependent upon the desired application. Examples of suitable electrolytes include aqueous solutions of salts. A preferred electrolyte is an aqueous solution of NaCl, having a concentration of less than 1 mole/liter (<1M), more preferably at about physiological concentration. Other electrolytes include salts of physiological ions including, but not limited to, potassium, ($K^+$), chloride ($Cl^-$), and phosphate ($PO_4^-$). The salt and its concentration may be selected as desired for particular applications. Other species may be selected by the skilled artisan for inclusion in the electrolyte reservoir. Such other reservoir species include, without limitation, chelation agents (e.g., citrate ions, EDTA) surfactants (e.g., non-ionic, cationic, or anionic), buffers, ionic excipients, osmolarity adjusters (e.g., polyethylene glycols, sugars), ionic antibiotics, penetration enhancers (e.g., alkanols), stabilizers, enzyme inhibitors, preservatives, thickening agents (e.g., acrylic acids, cellulosic resins, clays, polyoxyethylenes), and the like.

Alternatively, the electrolyte may comprise a material which is itself relatively immobile in the absence of an electric field, but which acts to deliver mobile ions in the presence of an electric field. In the latter case, the electrolyte may more properly be termed an "ion source." Examples of ion sources according to the invention include polyelectrolytes, ion exchange membranes and resins, non-ionic buffers which become ionic upon pH change, and other known ion sources.

Alternatively, the electrolyte reservoir may contain counterions that form a soluble salt with an electrochemically generated ion. For example, in an apparatus employing a silver anodal current distributing member, a suitable counterion might be acetate or nitrate. Such counterions are useful when other means are provided for sequestering electrochemically generated ions.

Thus, the electrolyte reservoir can provide at least one ion of the same charge as the electrochemically generated ion, to permit current to be conducted, and at least one oppositely charged ion.

C. The Ionized Substance (Drug) Reservoir

The reservoir structure of the iontophoretic apparatus of the invention further includes an ionized substance (protein or peptide) reservoir. The ionized substance reservoir must be in ionic communication with an epithelial surface.

The construction of the ionized substance reservoir must be consistent with the requirements for ionic communication with the epithelial surface and electrical communication with the current distribution member. Accordingly, the structure of the ionized substance reservoir would vary, depending upon the desired application. The ionized substance reservoir may include a liquid, semi-liquid, semi-solid, or solid material. With a flowable material, the ionized substance reservoir preferably further comprises means for at least substantially inhibiting the flow of the contents out of the reservoir. In such situations, the flow of the contents is desirably minimized when the device is in storage. For example, a membrane may be deployed to surround the contents of the ionized substance reservoir. In certain situations the flow of the contents of the reservoir may be minimized while in storage, but increased in use. For example, a surrounding membrane may increase in porosity, permeability, or conductivity upon the application of an electric field across the membrane. Examples of such membranes are disclosed in U.S. Pat. Nos. 5,080,546; 5,169,382; and 5,232,438, the disclosures of which are incorporated by reference herein.

In preferred embodiments, the ionized substance reservoir is constructed to retain its physical integrity and to inherently resist migration and loss of the ionized substance. Such embodiments include those in which the ionized substance reservoir includes a solid or semi-solid material such as a gel or other polymeric material. In an especially preferred embodiment, the ionized substance reservoir includes a polymeric film in which the substance to be iontophoretically delivered is dispersed. The mobility of the substance to be delivered is substantially increased by the application of the electric field, permitting effective delivery across the target epithelial surface. Such a film need not contain any significant amount of hydrating material. In preferred embodiments, a cross-linked hydrogel in the electrolyte reservoir, because it inherently contains significant amounts of water, can serve as a water reservoir during iontophoresis.

It may be desirable to provide the solution of active ingredient with a buffer. The ion of the buffer of like charge to the drug ion should have low ionic mobility. The limiting ionic mobility of this ion is preferably no greater that $1 \times 10^{-4}$ $cm^2$/volt-sec.

Additionally, as disclosed and claimed in U.S. patent application Ser. No. 60/026,862, filed Sep. 30, 1996, entitled: "Selectable Drug Delivery Profiles Using Competing Ions (Attorney Docket No. P-3730)", it may be desirable to control the flux profile of the drug being delivered by iontophoresis by adding to or having present in the reservoir containing the drug, ions which would compete with the drug ions for current (competing ions). To achieve various flux profiles for the drug being iontophoretically delivered, one may apply constant current but vary the concentration of the competing ions.

D. The Ionizable Substance (Protein or Peptide) for Iontophoretic Delivery

An ionic drug can be delivered from either the anode, the cathode, or both simultaneously. For example, if the ionic substance to be driven into the body is positively charged, then the positive electrode or anode will be the active electrode and the negative electrode or cathode will serve to complete the electrochemical circuit. Alternatively, if the ionic substance to be delivered is negatively charged, then the negative electrode will be the active electrode and the positive electrode will be the indifferent electrode. As discussed in greater detail herein the ionizable substance (protein or peptide) may have been previously modified to have an isoelectric point of less than about 4.0 or greater than about 7.3 with at least an electrostatic charge of plus or minus 1 over the pH range of about 4.0 to about 7.3 which is or is capable of being ionized.

E. Protective Backing

The iontophoretic apparatus of the invention may also include a suitable backing film positioned on top of the electrolyte reservoir. The backing film provides protection against contamination and damage to the current distributing member, if present, and the electrolyte reservoir of the apparatus.

F. Release Liner

The iontophoretic apparatus of the invention optionally includes a release liner which may fixed to the underside of the ionized substance reservoir by an adhesive. The release liner protects the surface of the ionized substance reservoir which contact the epithelial surface from contamination and damage when the device is not in use. When the device is ready for use, the release liner may be peeled off to expose the epithelial contacting surface of the ionized substance reservoir for application of the device to a patient.

G. Indifferent Electrode

Iontophoretic devices require at least two electrodes to provide a potential to drive drug ions into the skin of a patient. Both electrodes are disposed to be in intimate electrical contact with the skin thereby completing the electrochemical circuit formed by the anode pad and cathode pad of the iontophoretic device. The electrode pads may be further defined as an active electrode from which an ionic drug is delivered into the body. An indifferent or ground electrode serves to complete the electrochemical circuit. Various types of electrodes may be employed such as is described in United States application entitled Low-Cost Electrodes for an Iontophoretic Device, by Reddy et al., Ser. No. 08/536,029 filed Sep. 29, 1995.

The methods and compositions of the invention are not limited to practice with any one particular iontophoretic system or device. Generally, iontophoretic devices comprise at least two electrodes, an electrical energy source ( e.g., a battery) and at least one reservoir which contains the protein or polypeptide to be delivered. Several iontophoretic devices are known, such as those disclosed in P. Tyle, Pharmaceutical Research 3:318 (1986).

The reservoir or similar structure that contains the peptide or protein to be delivered can be in the form of any material suitable for making contact between the iontophoresis unit and the skin. Suitable materials include, but are not limited to, foams, gels, and matrices.

Iontophoresis gels can be karaya gum, other polysaccharide gels, or similar hydrophilic aqueous gels capable of carrying ions. Specific examples of such gels include polyvinyl alcohol, polymethyl pyrollidine methyl cellulose, polyacrylamide, polyhemia, polyhemia derivatives, and the like. The matrix selected should have non-irritating properties to avoid irritating the patient's skin or tissue, suitable conductivity properties to obtain good electrical contact with the skin or tissue, and the ability to act as a carrier medium for the peptides and proteins.

Other means for delivery of peptides and proteins include a patch comprising the peptide or protein as well as reusable or refillable iontophoretic devices.

In passing through the skin, from the outside stratum corneum to the inside basement membrane, it is well known that the drug molecule will encounter pHs from just below pH 5.0 to physiologic pH of 7.3 as shown in FIG. 1 (See e.g., Siddiqi et al. "Facilitated Transdermal Transport of Insulin" Journal of Pharmaceutical Sciences (1987) 76:4 p.341). If the isoelectric point is between pH 5.0 and pH 7.3, at some point during passage to the skin, the molecule will encounter a region where the local pH equals the isoelectric point. At this point, the molecule will have a zero net charge. Since the molecule requires a charge to move during Iontophoresis (as distinguished from electroosmosis), at this point the molecule has little mobility due to the electric field and the iontophoresis process is inoperable. Therefore, an isoelectric point outside the range of about pH 4.0 to pH 7.3 with an electrostatic charge of plus or minus 1 (absolute magnitude of 1) insures that virtually all the molecules will have a net charge, at all locations in the skin, and hence will move due to iontophoresis. An isoelectric point outside about pH 3–8.3 is preferred.

For example, natural insulin has an isoelectric point of 5.3. If it were placed in a reservoir at pH7, it would have a negative charge and would move away from negatively charged electrodes. As it moves into the skin, it will reach one of the places where the pH is 5.3. At this point, there will be no force on the molecule from the electric field since the molecule is uncharged. Further, at locations deeper in the skin, the pH can be (FIG. 1) lower. If the molecule diffused to this point, it would become positively charged and hence, move back toward the skin surface. At locations less deep in the skin, the pH can be higher. If the molecule diffused to this depth, it would have a negative charge, and now move away from the skin surface. Hence, nature has created a situation where the insulin can focus at one depth. Finally, at its isoelectric point the molecule is least soluble. Thus, not only will the molecule be focused at one location, it will tend to precipitate out.

Similarly, if the above insulin molecule were placed in a reservoir at pH 4, it would have a positive charge and would move away from positively charged electrodes. As it moves into the skin, it will reach one of the spots where the pH is 5.3. Again, at this spot the electric field will exert no force on the molecule. Further, at locations deeper in the skin, the pH can be higher. If the molecule diffused to this point, it would become negatively charged and move back toward the surface of the skin due to the electric field. At locations less deep in the skin due to the electric field. At locations less deep in the skin, the pH can be lower. If the molecule diffuses to this point, it will have a negative charge, and will move away from the surface of the skin due to the electric field. Hence, again, the molecule will focus at one location. In order to avoid this situation, molecules which are charged at one sign at all locations of the skin are preferred. Means to achieve this are, a) use a native molecule with an isoelectric point outside the pH of the skin or b) use a native molecule with an isoelectric point within the pH range of the skin and modified to obtain an analog with its isoelectric point outside the pH range of skin, i.e., below 4 and above 7.3.

Other characteristics for iontophoretic delivery of peptides and proteins include minimal size preferably the molecules should be in the monomer form and have the lowest molecular weight possible. Peptides and proteins have great difficulty penetrating the stratum corneum barrier, which many believe is due to their hydrophilicity, large molecular sizes and the lipophilic nature of the stratum corneum. If the molecule has a propensity to form polymers and aggregates, this has the effect of multiplying the molecular size by the degree of aggregation The isoelectric point and molecular size, in combination, increase the degree of mobility that a peptide or protein will have for iontophoretic delivery.

In addition, the peptides and proteins for iontophoretic delivery should preferably have high solubility in water (i.e., low partition coefficient). A peptide or protein with high solubility in water is generally referred to as hydrophilic. The peptides and proteins for iontophoretic delivery should preferably have both overall and local hydrophilicity. While overall hydrophilicity implies high water solubility, local hydrophilicity refers to that degree of interaction of portions of the molecule with lipophilic moieties in the skin High local hydrophilicity implies a low degree of interaction with lipophilic moieties in the skin, increasing the mobility with which the molecule will pass through the skin.

The ability of the peptides and proteins for iontophoretic delivery to maintain bioactivity is also highly desired. While modifications may lead to some loss of activity, as long as the intended result is achieved, loss of some bioactivity is acceptable. Trade-offs between achieving the most efficient, deliverable peptide and protein and achieving the most bioactive form of a peptide and protein will result in choosing the peptide or protein with properties closest to achieving the objectives desired.

Assemblages of amino acids refers to the variety of naturally occurring, modified forms of peptides and proteins and synthetic combinations of amino acid like residues, all of which may have biological activity. All assemblages of amino acids are suitable for use or suitable for modification for iontophoretic delivery in accordance with the present invention. Pro-drug forms and other forms where the biological activity remains and its ability to be delivered by iontophoresis is enhanced are also contemplated. Specific examples of suitable peptides and proteins include: Cardiovascular-active peptides and proteins such as Angiotension II antagonist, Antriopeptins, Bradykinin, and Tissue Plasminogen activator. CNS-active peptides and proteins such as Cholecystokinin (CCK-8 or CCK-32), Delta sleep-inducing peptide (DSIP), β-Endorphin, Melanocyte inhibiting factor-I, Melanocyte stimulating hormone, Neuropeptide Y and Nerve growth factor. GI-active peptides and proteins such as Gastrin antagonist, Neurotension, Pancreatic enzymes, Somatostatin and its analogs such as octreotide. Immunomodulating peptides and proteins such as Bursin, Colony stimulating factor, Cyclosporine Enkephalins, Interferon, Muramyl dipeptide, Thymopoietin, and Tumor necrosis factor. Metabolism-modulating peptides and proteins such as Human growth hormone, Gonadotropins, Insulin, calcitonin and its analogs such as elcatonin, Luteinizing hormone-releasing hormone (LHRH), Oxytocin, Thyrotropin releasing hormone (TRH), Calcitonin gene-related factor, and Vasopressins. Polypeptide growth factors such as Epidermal growth factor (EGF), Insulin-like growth factors I & II (IGF-I & II), Inter-leukin-2 (T-cell growth factor) (I1-2), Nerve growth factor (NGF), Platelet-derived growth factor (PDGF), Transforming growth factor (Type I or δ) (TGF), Cartilage-derived growth factor, Colonystimulating factors (CSFs), Endothelial-cell growth factors (ECGFs), Etythropoietin, Eye-derived growth factors (EDGF), Fibroblast-derived growth factor (FDGF), Fibroblast growth factors (FGFs), Glial Growth factor (GGF), Osteosarcoma derived growth factor (ODGF), Thymosin, Transforming growth factor (Type II or β) (TGF) and human parathyroid hormone (PTH).

Another method for altering the isoelectric point of a peptide or protein is by combination of the peptide or protein with at least one additional charged molecule, by means of hydrophobic bonding. Peptides and proteins have naturally occurring hydrophobic regions and the additional charged molecule contains both a charged region and a highly hydrophobic region, therefore, in aqueous solution, there is a natural attraction between the hydrophobic region of the molecule to be attached (the additional charged molecule) and the hydrophobic region(s) of the peptide or protein which results in their bonding. Examples of such charged molecules would be an anionic surfactant for lowering the isoelectric point and a cationic surfactant for raising the isoelectric point. As long as the molecule has both a charge and a hydrophobic region, it may be useful to achieve the goal of raising or lowering the isoelectric point of the peptide or protein by hydrophobic bonding.

This method of altering the isoelectric point of a peptide or protein is particularly attractive since this kind of bonding is concentration dependent. In an iontophoresis reservoir, at relatively high concentration, this bonding is preserved. However, after delivery of the combination molecule through the skin by iontophoresis, the combination molecule is a relatively low concentration while circulating through the body, so the two molecules will separate, leaving the biologically active peptide or protein in its natural and potent state.

The ability to modify a peptide or protein to its minimal size is readily achievable. For example, it is known that human growth hormone-releasing factor (hGRF) is a forty-four amino acid long peptide (hGRF (1-44)-NH2)) that displays high potency with the carboxy terminus deleted (hGRF(1-29)-NH2), see A. M. Felix, Pharmaceutical Technology, May 1991 (page 28). In general, smaller portions of large peptides are available through direct synthesis. These fragments can then be tested for the appropriate bioactivity. Traditionally, fragment peptides are synthesized "one-at-a-time" by automated solid phase synthesis. Recently, however, rapid methods of multiple peptide synthesis have become available which facilitate this process (Houghten, R. A., Proc. Nat'l, Acad. Sci. USA 82 (1985) 5131.

The isoelectric point (pI) of a bioactive peptide can be adjusted by several methods. One method is to substitute specific undesirable residues for more desirable ones. For instance, to raise the pI of a peptide, one would remove or exchange negatively charged residues such a glutamate or aspartate residues, replacing them with neutral or positively charged residues such as lysine or arginine. Neutral residues such as glycine and proline, can be replaced with positively charged residues such as lysine and arginine. Charged residues could also be conveniently added to the amino or carboxy terminii of the peptide chain by direct solid phase synthesis.

Another method involves developing a pro-drug of the peptide of interest. For instance, negatively charged side chains of aspartic acid, glutamic acid, or the carboxy terminus could be esterified with a neutral or positively charged group which is subsequently removed in vivo, restoring the original peptide structure.

Peptide and protein modifications may be realized by a number of routes. Direct chemical modifications are one possible path (see Lundblad, R. L., Chemical Reagents For Protein Modification, (1991), CRC Press, Boca Raton, Fla.). Site directed mutagenesis of nucleic acids and subsequent expression of the proteins is another route. The use of automated peptide synthesis techniques extends the range of possibilities since un-natural amino acids can be incorporated into the peptide/protein. Modification by the use of enzymes is a fourth method of developing analogues. Enzymes which carry out a range of post-translational modifications are known. Among the protein modifying enzymes are carboxylases, phosphate kinases, hydroxylases and glycosylases. The above modification techniques can be used either alone or in combinations to achieve the desired results in terms of isoelectric point, total charge, and bio-activity.

These methods of adding or altering the charge characteristics of peptides often improve their solubility characteristics as well. Proteins with isoelectric points outside the range of 4 to 7.4 will not likely precipitate or aggregate during transit through the skin. Means for modifying peptides and proteins to obtain molecules with positive charges through the isoelectric point from about 4 to about 7.4 include sulfation. Sulfated proteins can be prepared by any of several methods described in the literature. Under appropriate conditions, sulfonate groups are specifically appended to aliphatic hydroxyl groups such as are found on serine and threonine residues Insulin, for example, has been sulfated by treatment with concentrated sulfuric acid, either alone or in conjunction with a dehydrating agent such as carboduimide (Reitz, H. C., Ferrel. R. E., Fraenkel-Conrat, H., et al (1946) J. Am Chem. Soc., 68 1024–1031 and Cerami, A., Pongor, S. Brownlee, M. (1985) U.S. Pat. No. 4,534,894). Pyridium sulfonic acid was also used to introduce sulfate groups to insulin (Sluyterman L. A. A. E., Kwestroo-Van den Bosch, J. M. (1960) Biochem. et Biophys. Acta, 38, 102–113). Such procedures should work on all the native insulins such as human, porcine, and bovine, their synthetic molecules and analogs thereof As depicted in FIG. 6 an embodiment of the iontophoretic device of this invention 50 is configured as follows: an anode patch 10, having an anode electrode compartment 11 in ionic communication with a skin contacting compartment 13. The skin contacting compartment 13 and the anode electrode compartment 11 maybe separated by a compartment separation means (membrane) 17. The anode electrode compartment 11 also contains an anode 14 and an electrolyte (anolyte) 15. The skin contacting compartment is attached to the patient's skin 36. A cathode patch 20, having a cathode electrode compartment 21 in ionic communication with a skin contacting compartment 23. The skin contacting compartment 23 and the cathode electrode compartment 21 maybe separated by a compartment separation means (membrane) 27. The cathode electrode compartment 21 also contains an cathode 24 and an electrolyte (catholyte) 25. The skin contacting compartment is attached to the patient's skin 36.

The following examples illustrate the specific embodiments of the invention described in this document. As would be apparent to skilled artisans, various changes and modifications are possible and are contemplated within the scope of the invention described.

EXAMPLE 1

Preparation of monomeric insulin with pI>7

A monomeric insulin such as the des-pentapeptide (B26–30) free acid or amide is prepared enzymatically using established literature procedures. To this base material is coupled a peptide such as lysyl-lysine, carrying a suitable number of charged groups.

Experimental Porcine insulin (Calbiochem Corp., La Jolla, Calif.) is cleaved with trypsin to produce the des-octapeptide (B23–30) analogue. This material is coupled with H-Gly-Phe-Phe-NH2 using trypsin assisted catalysis in mixed aqueous-organic systems following established procedures (Nakagawa S. H., Tager, H. S. (1986)) J. Biol. Chem., 261, 7332–7341). The resulting des-pentapeptide (B26–30) insulin is purified by ion exchange chromatography.

The dipeptide N-(Boc)-$\epsilon$-Boc-lysyl-$\epsilon$-Boc-lysine is prepared by coupling N-(Boc)-$\epsilon$-Boc-lysine N-hydroxy succinimide ester with $\epsilon$-Boc-lysine in anhydrous dimethyl formnamide. The reaction is allowed to stir overnight evaporated in vacuo, and taken up in ethyl acetate. The organic layer is washed with aqueous citric acid, water, and dried. The resulting oil is triturated with hexane to yield a solid product.

The dipeptide is then coupled to des-pentapeptide insulin using an established fragment coupling technique (Kisfaludy L., Roberts, J. E., Johnson, R. H., et al. (1970) J. Org. Chem. 35, 3563–3565). The pentafluorophenyl ester of the dipeptide is prepared in situ by treatment with one equivalent of the dicyclohexylcarbodiimide-pentafluorophenol "complex" in dimethylformamide at 0° C. The reaction is allowed to warm slowly to room temperature over a period of 1 hour. The solution is filtered to remove the precipitated dicyclohexyl urea, and added to a solution of insulin in dimethylformamide. The activated dipeptide is added in a 10-fold molar excess. The reaction is stirred for 4 hours at room temperature, at which time diethyl ether is added to precipitate the protein. The precipitate is recovered by centrifugation and treated for 1 hour with anhydrous trifluoroacetic acid to remove the Boc protecting groups. Following removal of the acid in vacuo, the product is purified by ion exchange chromatography on sulfonated sepharose in 20% acetic acid, using a sodium chloride gradient to dilute the proteins.

The product of this sequence of reactions is an insulin analogue carrying a lysyl-lysine dipeptide appended to the N-terninal positions of the A and B chains The pI of this monomeric analogue is 8.4.

EXAMPLE 2

Lack of Transport of Insulin—pI=5.3
The following examples have been taken using the porcine skin flap model (J. Riviere et al., Fund. Appl., Toxicol. 7:444 (1986) to study transdermal transport:
Two skin flaps
Duration of iontophoresis 4 hrs at 0.9 ma DC
Cathode dosing solution—regular insulin (Eli Lilly, Indianapolis, Ind.)>100 Units/ml, PI 5.3
Anode solution 10% saline
Area of electrode 4.5 cm$^2$—Porex™ reservoir with Ag mesh anode
Current density 200 $\mu$/cm$^2$
Samples of perfusate taken every 30 minutes starting with one hour prior to iontophoresis until 4 hours after iontophoresis. Specimens analyzed using insulin RIA—sensitive to 10 $\mu$U/ml (400 programs/ml) (Cambridge Research, Boston, Mass.)
Result—all samples had concentrations of insulin below minimally detectable levels.

EXAMPLE 3

Figure 1:
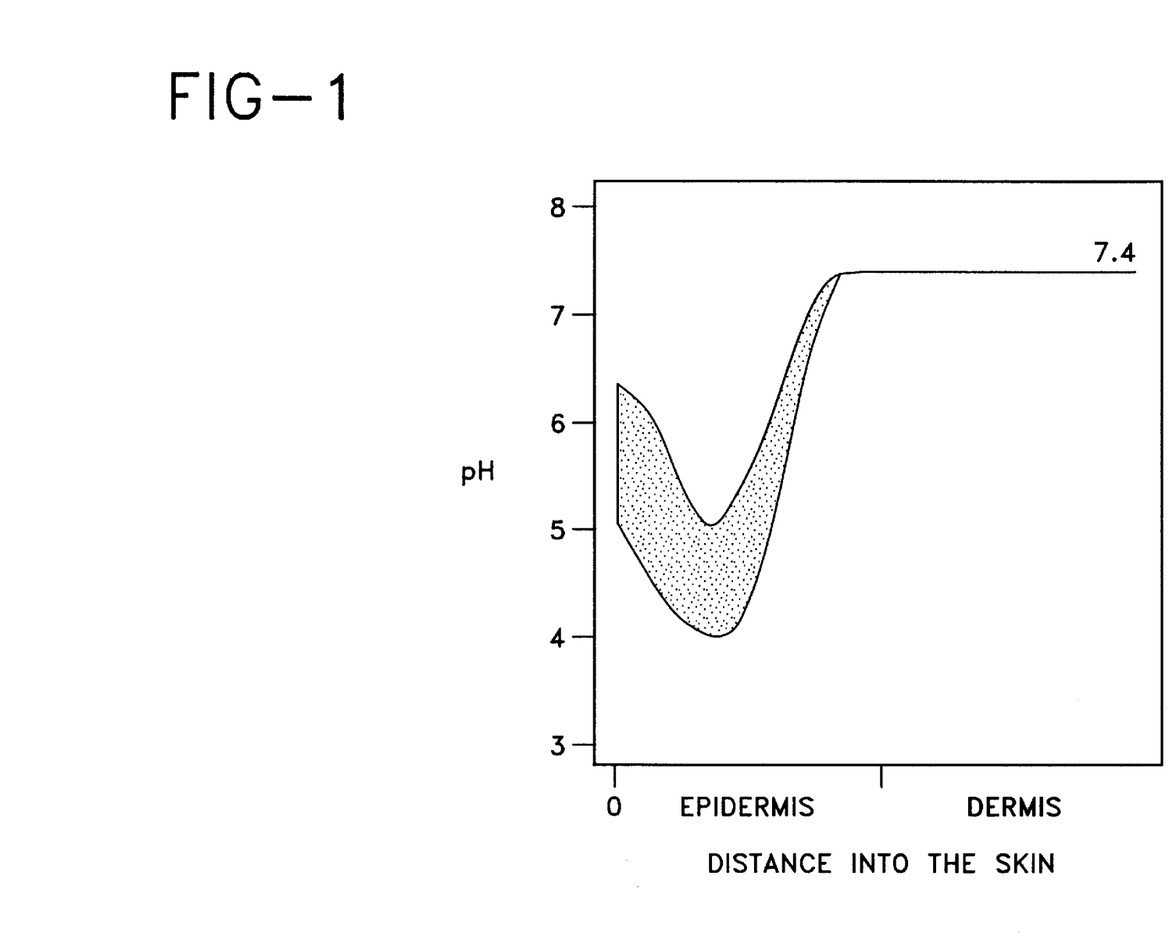
FIG. 1 is a schematic of skin pH versus skin depth.
Figure 2:
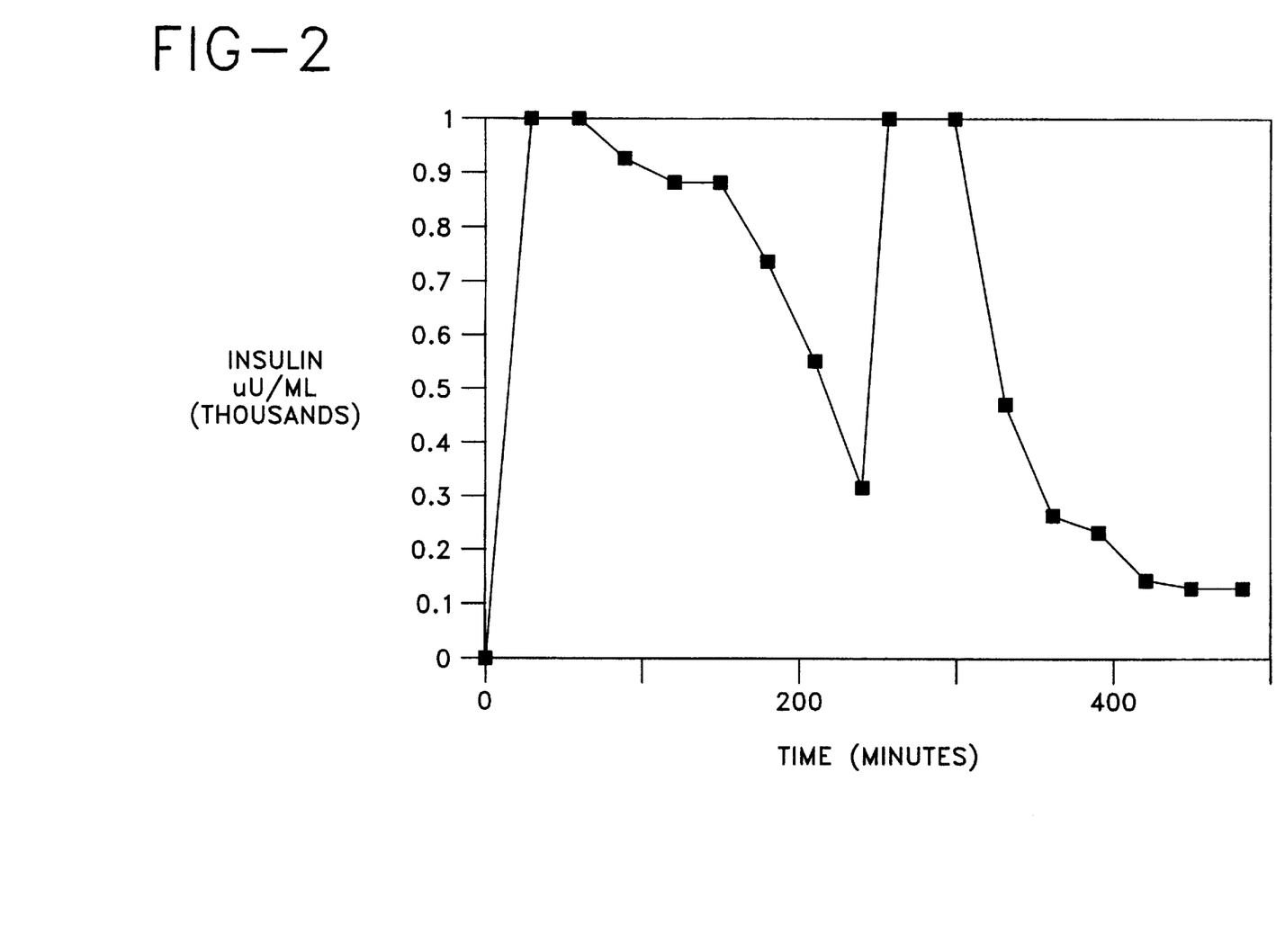
FIG. 2 is a schematic of a skin flap experiment demonstrating iontophoretic delivery of a sulfated insulin.

Transport of sulfated insulin pI=1.0
Two skin flaps
Duration of iontophoresis—4 hours at 0.9 ma DC
Cathode dosing solution—sulfated insulin (Connought Labs, Toronto, Canada), 100 U/ml, pI —1.0
Anode solution 10% saline
Area of electrode 4.5 cm$^2$—Porex ™ reservoir with Ag/AgCl mesh cathode
Current density 200 $\mu$A/cm$^2$
Samples of perfusate taken every 30 minutes starting with one hour before Iontophoresis until 4 hours after iontophoresis.
Specimens analyzed using insulin RIA (Cambridge Research, Boston, Mass.) sensitive to 10 $\mu$U/ml (400 programs/ml).
Result: See FIG. 2—significant transport of insulin analog (sulfated insulin)

EXAMPLE 4

Thyrotropin releasing hormone (TRH) has a pKa of approximately 6.2. It carries decreasing (positive) charge over the pH range 5–7, being essentially +1 charged at the low pH and progressing toward being uncharged at pH7. Although delivery of this compound under the influence of an electric field has been documented, the fluxes indicated that the drug was carried passively by convection (Burnette, R. R., et al., J., Pharm. Sci., 75, (1986), 738–743.)

Figure 4:
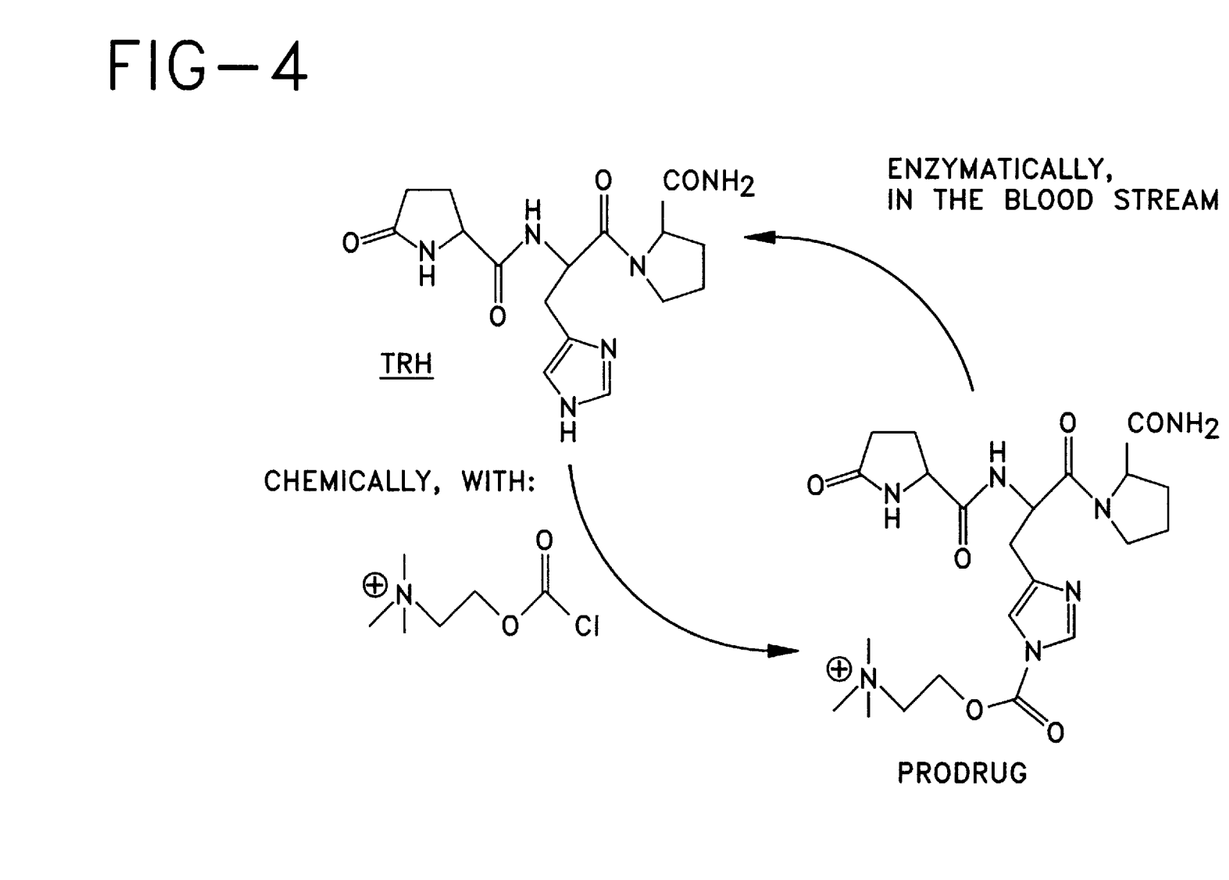
FIG. 4 is a schematic of the formation of an LHRH pro-drug.

A pro-drug of TRH which carries a positive charge over the pH range of 4–7 can be prepared using the methods of Bundgaard, et al. (Pharm. Res 7 (1990), 885–892.). In a modification of the method cited, choline chloroformate (formed from choline and phosgene) is substituted for the hydrophobic chloroformates in the synthetic procedure (See FIG. 4) This substitution leads to a TRH pro-drug with a quaternary amine functionality which maintains a +1 charge at all pH's. This compound will exhibit high water solubility and will remain charged over the pH range of 4–7.

EXAMPLE 5

Figure 3:
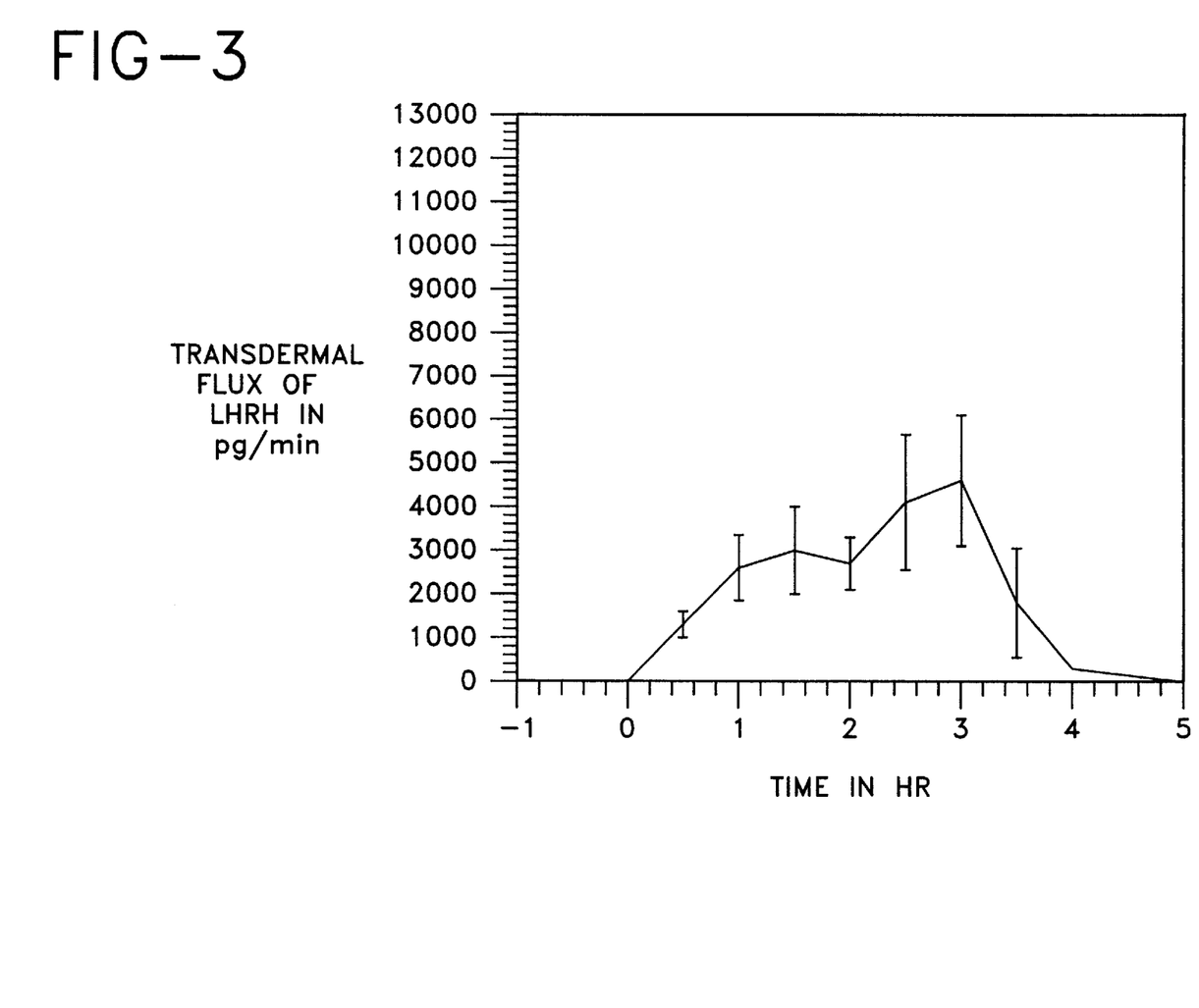
FIG. 3 is a schematic of a skin flap experiment demonstrating iontophoretic delivery of LHRH.

Iontophoretic delivery of LHRH (pI-11) using the skin flap model of J. Riviere
Electrodes—Porex™ sandwich 1 cm$^2$ with Ag anode mesh made by Becton Dickinson Research Center LHRH (Luteinizing hormone releasing hormone) solution: 1 mgm/ml in 154 mM NaCl plus 10 mM MES buffer pH6.0.
Indifferent electrode solution: NaCl 159 mgm/ml
Iontophoresis current 0.2 ma for 3 hours
FIG. 3—mean ±ISD for six replicate skin flaps
Source of LHRH: Sigma Chemical Co., St. Louis, Mo.

EXAMPLE 6

Delivery of PTH (1–34) Amino Acids
Subcutaneous delivery
Human PTH amino acids was re-hydrated in sterile saline to an approximate concentration of 100 micrograms per milliliter. Dosages were later calibrated by immunoradiometric assay ("IRMA"). In the example, the dosing solution was 137.1 ug/ml. Of this solution, 0.25 ml were injected subcutaneously behind the ear of weanling yorkshire swine. This site was chosen because the skin is relatively thin and loose compared to the rest of the animal. Bleeds were taken at time zero and at subsequent 30 minute intervals, for a total of 4 hours. The specimens were centrifuged and the resulting plasma was aspirated and immediately frozen on dry ice. They were kept frozen until the assay was started, which was on the same day as the experiment. Assay results of these subcutaneous injections are shown in FIG. 5, open symbols on the graph.

Iontophoretic Delivery
Human PTH (1–34) amino acids was re-hydrated in 10 mM MES, 10 mM NaCl, 0.01% TRITON™ X-100, pH 6 to an approximate concentration of 10 mg/ml; later calibrated in the IRMA. One hundred fifty microliters of the drug were loaded into a 4 cm² 1/32 inch DBS (Hydrophilic) Porex™ reservoir, then inserted into an anodal patch containing formulation buffer, IRP-69 ion exchange beads and 2% agarose. The patches were applied to the flank of weanling swine and 2 mA (500 uA/cm²) were applied for 4 hours. During that time, and for two subsequent hours, plasma specimens were taken at 30 minute intervals.

Figure 5:
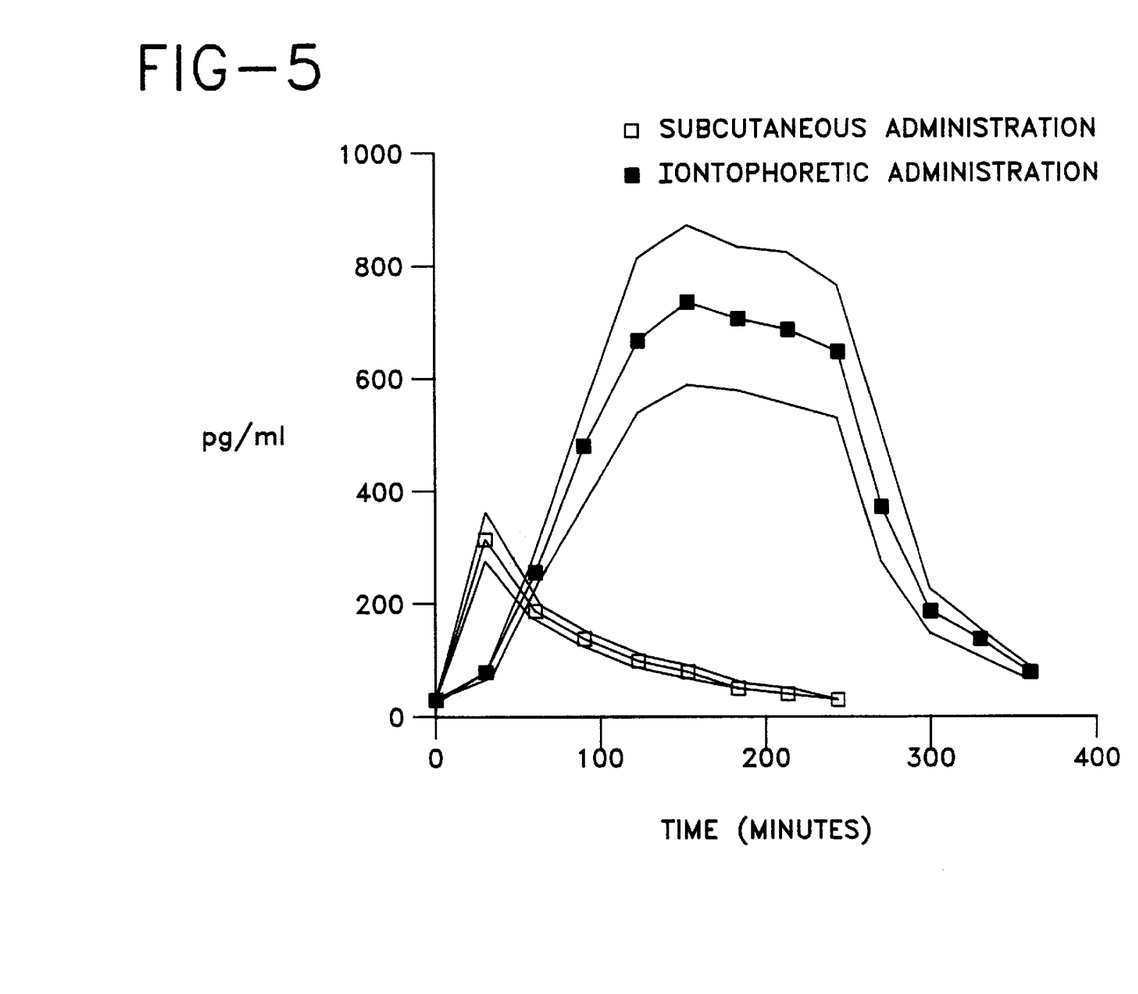
FIG. 5 is a graph depicting programs per milliliter of Human PTH versus time for assay results of subcutaneous injections, as well as serum versus time following iontophoretic delivery of Human PTH.
Figure 6:
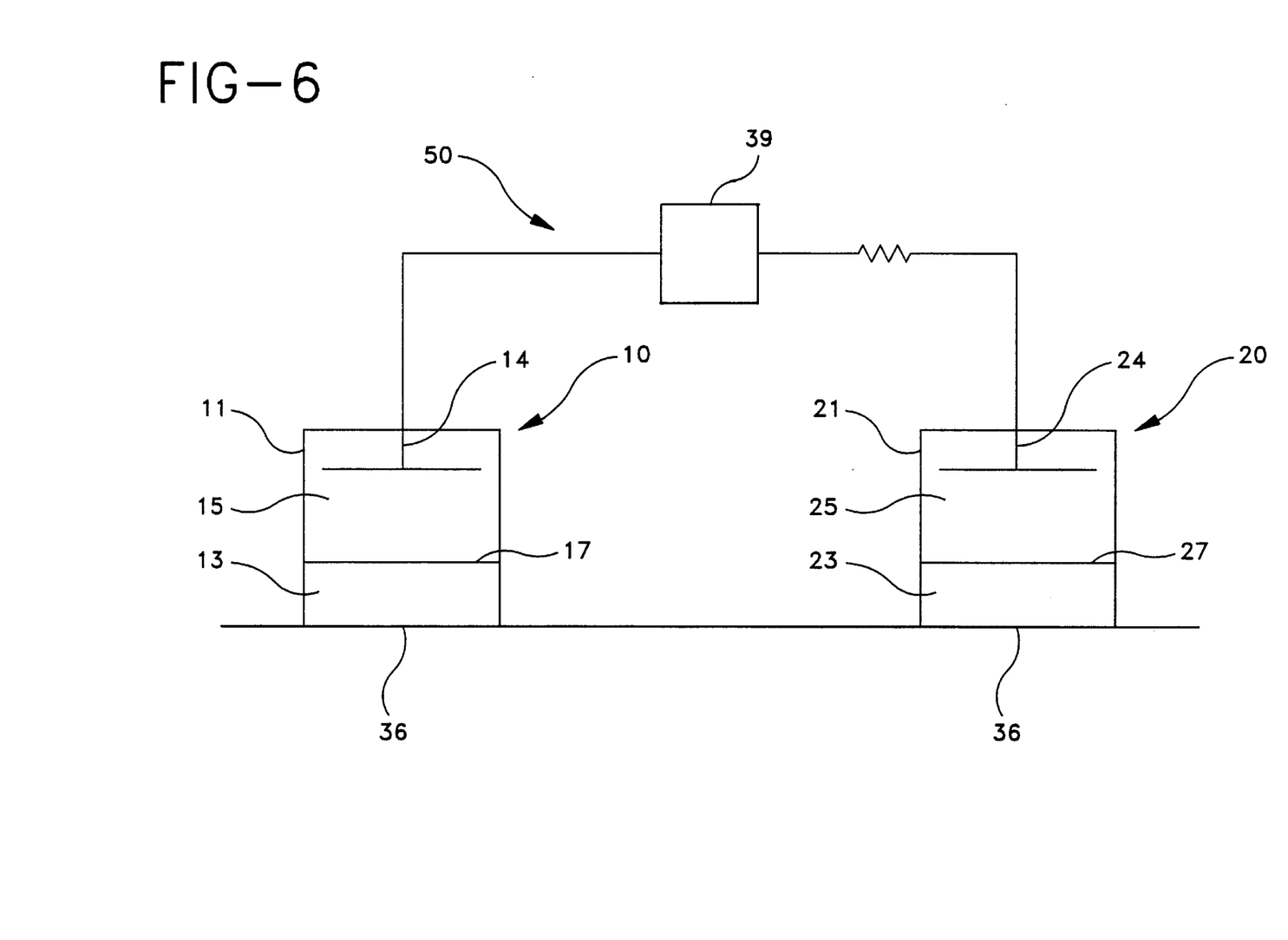
FIG. 6 depicts an iontophoretic device embodying the present invention.

FIG. 5, closed symbols on the graph, show the serum concentration as determined by the IRMA for N=8 Yorkshire weanling swine of approximately 25 Kg when the PTH concentration in the patch was 6.87 mg/ml and 9.45 mg/ml, respectively.

Note that PTH (1–34) amino acids was specifically selected because of the favorable pI (8.4) and the charge of at least +1 over the pH range of 4–7.3. This data clearly shows that iontophoresis of PTH (1–34) amino acids has delivered in excess of the human therapeutic dose represented by the subcutaneous injections.

What is claimed is:

1. An iontophoretic device for non-invasively administering a therapeutic dose of a modified protein or peptide to a patient comprising:

a) a current distributing member;

b) an ionized substance reservoir containing the modified protein or peptide in an ionized or ionizable form, in electrical communication with the current distributing member and adapted to be placed in ionic communication with an epithelial surface, wherein the modified protein or peptide is a modification of a protein or peptide that has had its isoelectric point changed from either a value greater than about 4.0 to a value less than 4.0 or from a value less than 7.3 to a value greater than 7.3 and has an electrostatic charge of at least plus or minus 1 over the pH range of human skin, of about 4.0 to about 7.3;

c) an electrolyte reservoir containing an electrolyte in electrical communication with an indifferent electrode;

d) an electrical power source in current delivering connection with the current distributing member and the electrolyte reservoir.

2. The iontophoretic device of claim 1 wherein the isoelectric point of the modified protein or peptide is less than about 3.0 or greater than about 8.3.

3. The iontophoretic device of claim 1 wherein the modified peptides or proteins have a water solubility factor greater than about 1 mg/ml.

4. The iontophoretic device of claim 1 wherein the peptides or proteins is insulin.

* * * * *